Figure 1C:
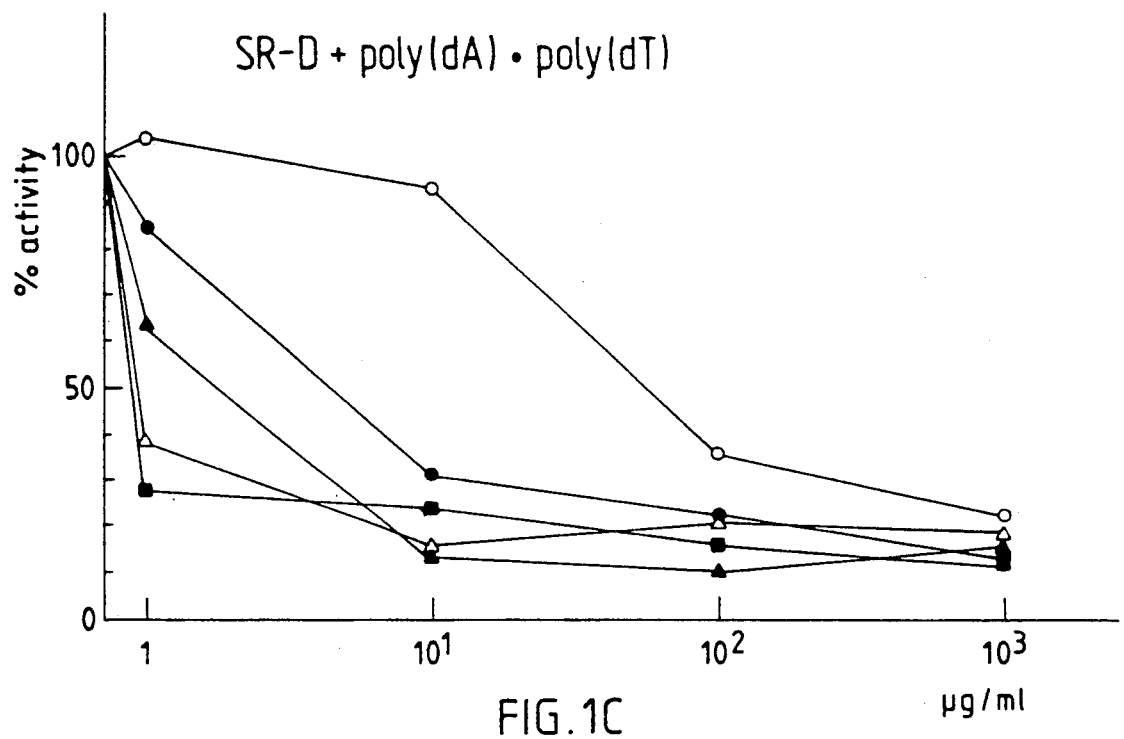

United States Patent [19]

Diringer et al.

[11] Patent Number: 5,153,181

[45] Date of Patent: Oct. 6, 1992

[54] PHARMACEUTICAL COMPOSITIONS COMPRISING ORGANIC POLYMERS CONTAINING INORGANIC ANIONIC GROUPS AND METHOD OF PROPHYLAXIS AND TREATMENT OF RETROVIRUS INFECTIONS IN MAMMALS USING SAID COMPOSITIONS

[75] Inventors: Heino Diringer; Karin Mölling, both of Berlin, Fed. Rep. of Germany

[73] Assignees: Max-Planck-Gesellschaft Zur Forderung der Wissenschaft E.V.; The Federal Republic of Germany as represented by the Federal Minister of Youth and Health, both of Fed. Rep. of Germany

[21] Appl. No.: 4,079

[22] Filed: Jan. 16, 1987

[30] Foreign Application Priority Data

Jan. 16, 1986 [DE] Fed. Rep. of Germany ....... 3601136

[51] Int. Cl.$^5$ ..................... A61K 31/715; C08B 37/00
[52] U.S. Cl. ......................................... 514/54; 514/59; 514/885; 536/54; 536/112; 536/123
[58] Field of Search .......................... 536/112, 123, 54; 514/59, 54, 885

[56] References Cited

U.S. PATENT DOCUMENTS

| | | | |
|---|---|---|---|
| 4,066,829 | 1/1978 | Nair et al. ............................ | 536/112 |
| 4,357,326 | 11/1982 | Nair et al. ............................ | 536/54 |
| 4,489,065 | 12/1984 | Walton et al. ........................ | 536/54 |
| 4,490,525 | 12/1984 | Hayatsu et al. ...................... | 536/54 |
| 4,590,181 | 5/1986 | McCarthy ............................ | 536/112 |
| 4,640,912 | 2/1987 | Hausman ............................. | 536/54 |
| 4,695,624 | 9/1987 | Marburg et al. ..................... | 536/1.1 |
| 4,772,547 | 9/1988 | Heimer et al. ....................... | 435/5 |
| 4,783,446 | 11/1988 | Neushul ............................... | 514/54 |
| 4,795,739 | 1/1989 | Lifson et al. ......................... | 514/8 |
| 4,806,352 | 2/1989 | Cantrell .............................. | 514/937 |

FOREIGN PATENT DOCUMENTS

| | | |
|---|---|---|
| 3124384 | 1/1983 | Fed. Rep. of Germany . |
| 51-41083 | 4/1976 | Japan . |
| 918/83 | 1/1986 | Japan . |

OTHER PUBLICATIONS

Certified English translation of German Priority Document P 36 01 136.3.
U.S. patent application Ser. No. 801,115 filed Nov. 22, 1985 by Michael Neushul.
Ueno and Kuno, *Lancet I*, p. 1397 (1987).
Baba et al., *Antiviral Res.* 9:335-343 (1988).
Biesert et al., *AIDS* 2:449-457 (1988).
Thiele et al., *Eur. J. Immunol.* 10:1161-1164 (1989).
DiCioccio et al., *Cancer Res.* 36:2401-2407 (1976).
Rojko et al., *J. Natl. Cancer Inst.* 67:899-910 (1981).
Schaffrath et al., *Hoppe-Seyler's Z. Physiol. Chem.* 357:499-508 (1976).
De Somer et al., *J. Virol.* 2:886-893 (1976).
The European Search Report for the corresponding European Patent Application No. 87/00477.6.
Mongraph 1848, *The Merck Index*, Merck & Co., Inc. Rahway, N.Y. (1983).
Suzuki, *Chemical Abstracts* 86:375 (1977).
Schaffrath et al., *Hoppe-Seyler's Z. Phsiol. Chem.* (1976) pp. 499-508.
Schaffrath et al., *Chemical Abstracts* 85:254 (1976).
Kiehl et al. *Chemical Abstracts* 81:27 (1974).
DiCioccio et al., *Chemical Abstracts* 89:23 (1978).
Fukumi et al. "The Mechanism of Anti-Viral Action of Interferon," *Research of Virus* pp. 276-287.
de Gruyter et al. (ed.) *W. Pschyrembel Klinisches Worterbuch*, pp. 1280-1281 (1982).
Fields et al., (ed.) *Virology* (1985) pp. 1519-1520.
Oberg, *Pharmac. Ther.*, 19:387-415 (1983).
Sundquist et al., *J. Gen. Virol.*, 45:273-281 (1979).
Mitsuya et al., *Science*, 226:172-174 (1984).
Ehlers et al., *J. Gen. Virol.*, 65:423-428 (1984).
Ehlers and Diringer, *J. Gen. Virol.*, 65:1325-1330 (1984).

*Primary Examiner*—Ronald W. Griffin
*Assistant Examiner*—Nancy S. Carson
*Attorney, Agent, or Firm*—Birch, Stewart, Kolasch & Birch

[57] ABSTRACT

The subject matter of the invention is the use of organic polymers which contain inorganic anionic groups for prophylaxis and therapy of retrovirus infections in mammals.

11 Claims, 4 Drawing Sheets

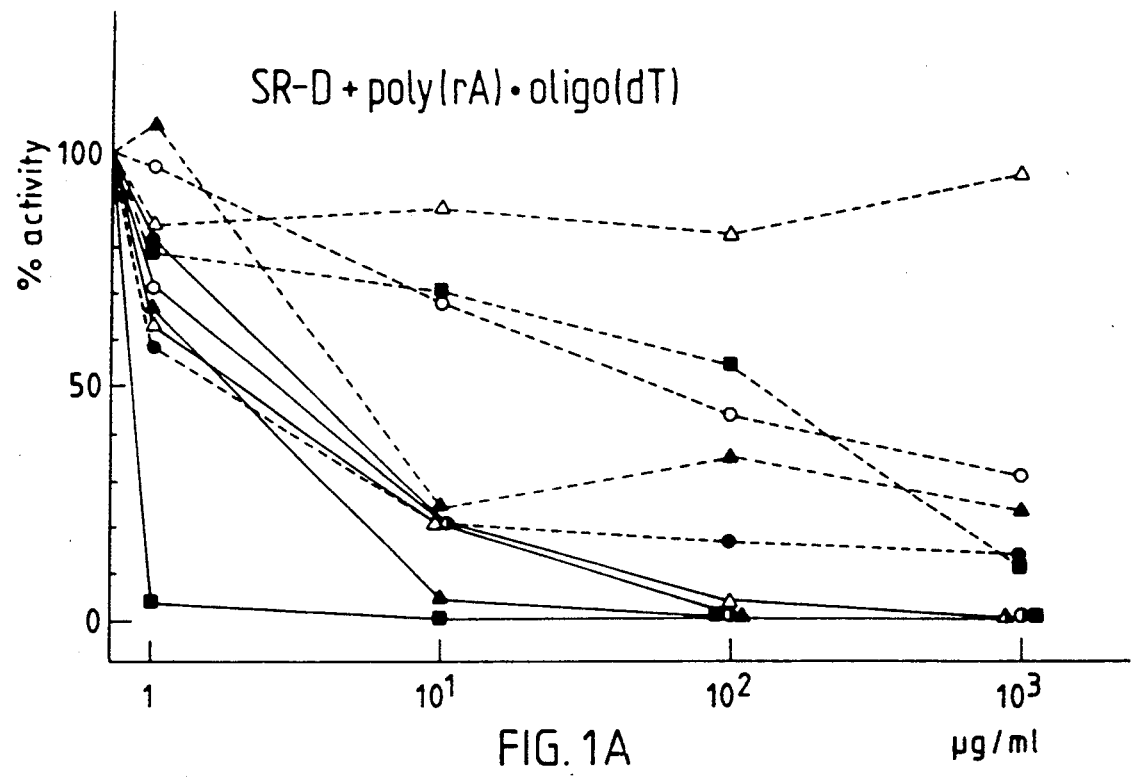
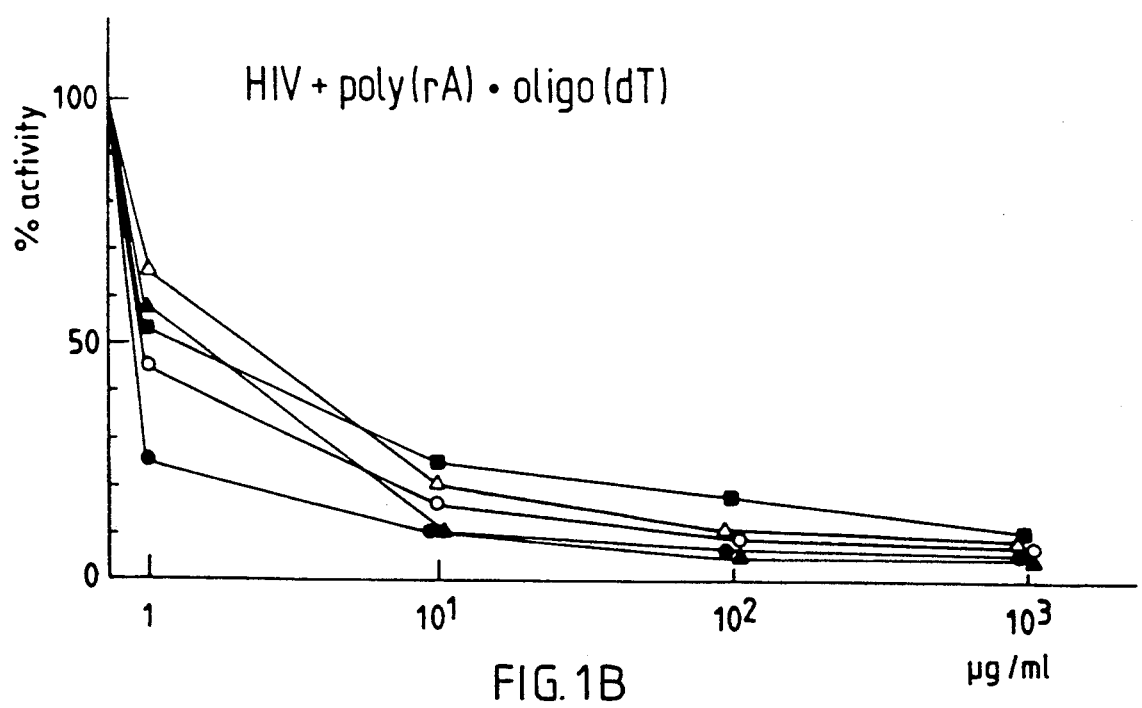

PHARMACEUTICAL COMPOSITIONS COMPRISING ORGANIC POLYMERS CONTAINING INORGANIC ANIONIC GROUPS AND METHOD OF PROPHYLAXIS AND TREATMENT OF RETROVIRUS INFECTIONS IN MAMMALS USING SAID COMPOSITIONS

DESCRIPTION

1. Technical Field

The invention relates to the use of organic polymers containing inorganic anionic groups for prophylaxis and therapy of retrovirus infections.

2. Background Art

The genetic information of retroviruses is contained in a ribonucleic acid (RNA). During replication in an infected cell the viral genome is transcribed into a copy of deoxyribonucleic acid (DNA). This RNA-depending synthesis of DNA is performed by reverse transcriptase, a retrovirus specific enzyme encoded by the viral genome. Reverse transcriptase is an integral part of the virion.

Oncogenic tumor viruses cause leucemia and other malignant cell growths in man and a variety of animal species. Nononcogenic retroviruses, also called lentiviruses, cause chronic and relapsing diseases In man and animals. In particular, AIDS (Aquired Immuno Deficiency Syndrom)in man is caused by retroviruses, for example LAV/HTLV III (recently called HIV).

A selective protection against virus replication and consequently against the disease may be obtained in man and other mammals by inhibiting specifically the viral RNA-depending synthesis of DNA carried out by the virus-coded reverse transcriptase. The most important known inhibitors of reverse transcriptase are foscarnet and suramin. Foscarnet as an inhibitor of reverse transcriptase is known from B. Oberg "Antiviral effects of phosphonoformate (PFA, Foscarnet Sodium)" Pharmac. Ther. 19 (1983), 387–415 and from B. Sundquist et al., "Phosphonoformate Inhibits Reverse Transcriptase", J. gen. Virol. 45 (1979) 273–281.

The chemical structure of foscarnet is:

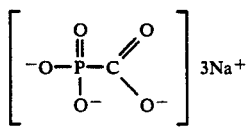

Because of the considerable toxicity exhibited by this compound in clinical trials, foscarnet is not acceptable for prophylactic or therapeutic use in retrovirus infections.

The action of suramin as an inhibitor of reverse transcriptase has been described by Mitsuya et al. "Suramin Protection of T-Cells in Vitro Against Infectivity and Cytopathic Effect of HTLV-III", Science 226 (1984), 172–174. Suramin is used as a drug for treatment of African tryponosomiasis. Its chemical structure is given as:

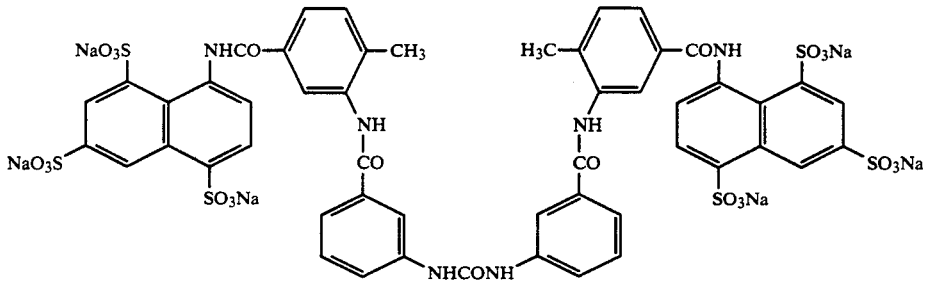

Again as in the case of foscarnet according to clinical trials, Suramin is too toxic for the mammalian organism at concentrations that are necessary for prophylactic and therapeutical treatment of retrovirus infections.

SUMMARY OF THE INVENTION

Thus, it is an object of the present invention to provide inhibitors of reverse transcriptase which as compared to the known inhibitors of this enzyme exhibit less side effects on the mammalian organism and thus are suitable for prophylactic and therapeutical use in retrovirus infections.

It is a further object of the invention to provide a pharmaceutical composition which is useful for prophylaxis and therapy of retrovirus infections. Another object of the invention is to provide a method of producing a pharmaceutical composition which can be used in the prophylaxis and therapy of retrovirus infections. Still another object of the invention is to provide a method of prophylaxis and treatment of retrovirus infection without causing the undesirable side effects exhibited by the use of the known inhibitors of reverse transcriptase.

These objects of the invention have been achieved by the surprising finding that organic polymeric compounds containing inorganic anionic groups exhibit effective inhibition of reverse transcriptase, without showing the undesirable side effects of the known inhibitors of said enzyme.

Thus, one subject matter of this invention is the use of organic polymeric compounds containing inorganic anionic groups for prophylactic and therapeutic treatment of retrovirus infections of mammals.

Another subject matter of the invention is a pharmaceutical composition which is useful for the prophylaxis and therapy of retrovirus infections in mammals said composition comprising at least one organic polymeric compound containing inorganic anionic groups in an amount sufficient to provide efficient prophylaxis or therapeutical effects against retrovirus infections in mammals in combination with a pharmaceutical carrier.

A further subject matter of the invention is a method for preparing a pharmaceutical composition which is useful for the prophylaxis and therapy of retrovirus infections in mammals said method comprising combining at least one organic polymeric compound containing inorganic anionic groups with a pharmaceutical carrier.

Still a further subject matter of the invention is a method of prophylaxis and treatment of retrovirus infections in mammals said method comprising administering to a patient requiring said treatment at least one organic polymeric compound containing inorganic anionic groups in an amount sufficient to provide efficient prophylactic or therapeutical effects against retrovirus infections.

BEST AND VARIOUS MODES FOR CARRYING OUT THE INVENTION

Examples for organic polymeric compounds containing inorganic anionic groups which can be used according to the invention are polyvinyl sulfates, polyvinyl phosphates or anionic polymeric carbohydrates. According to a preferred embodiment of the invention the organic polymeric compounds are carbohydrates without carboxyl (—COOH) and amino (—NH$_2$) groups.

In another preferred embodiment of the invention the polymeric carbohydrates are composed of monomeric pentoses such as ribulose, arabinose or xylose, and their derivatives.

Preferably, the monomeric form is xylose, a more preferred form being the pyranose configuration of xylose. Even more preferably, the polymer of pentoses is a pentosan polysulfate.

In another preferred form the polymeric carbohydrate is composed of monomeric hexoses such as mannose, fructose, sorbose, galactose or glucose, and their derivatives. Preferably the monomeric form is glucose. A more preferred form is the pyranose configuration of glucose. Most preferably, the polymer is a dextran sulfate with a molecular weight (MW) of at least 6,000.

In the invention special examples for organic polymers containing inorganic anionic groups are dextran sulfate MW 500,000, dexran sulfate MW 8000, and pentosan polysulfate MW 5000.

Dextran sulfate is a polyester of dextran with sulfuric acid. Dextran can be obtained from bacteria like Leuconostoc or other Lactobacteria which synthesize dextran from saccharose. Dextran contains α-D-glucose subunits, predominantly linked by α-1,6-glycosidic bonds.

Pentosan polysulfate is a polyester of sulfuric acid and β-D-xylopyranose with 1,4-glycosidic bonds.

Hereinafter, the invention is exemplified with dextran sulfates MW 8,000 and 500,000, and pentosan polysulfate MW 5,000.

These substances have already been used in medicine as anticoagulants proving their pharmacological compatibility. In addition, the effect of dextran sulfate MW 500,000 on unconventional virus infections resulting in spongiform encephaopathies is known (Ehlers et a. "The Reticuloendothelial System in Scrapie Pathogenesis", J. gen. Virol. 65 (i984) 423–428; Ehlers and Diringer "Dextran sulfate 500 Delays and Prevents Mouse Scrapie by Impairment of Agent Replication in Spleen", J. gen. Virol. 65, 1325-1330; Diroinger "Ein Modell für Alterungsprozesse und degenerative biochemIsche Veränderungen im Gehirn - Scrapie", Funkt. Biol. Med. 4 (1985) 129–140) Finally, the inhibitory effect of dextran sulfate MW 500,000 on the replication of encephalo-myocarditis (EMC)-virus, ECHO-virus, Coxsackie A9-virus and herpes virus is known.

These known effects of dextran sulfate MW 500,000 as well as of the other substances with which this invention is concerned, in no way suggest the use of organic polymeric compounds with inorganic anionic groups as inhibitors of reverse transcriptase and thus as prophylactic and therapeutic drugs in retrovirus infections. In blood clotting as well as in the virus infections mentioned above the RNA-depending DNA synthesis through a virus-coded and virus-specific reverse transcriptase plays no role at all. Therefore, the known effects of these substances did not allow to deduce a specific inhibitory effect on the reverse transcriptase of retroviruses.

Specific inhibition of the RNA-dependent DNA polymerase by the compounds used in the present invention (in the following called the "here described compounds") is analyzed with a model virus system, avian Schmidt-Ruppin D (SR-D) virus, which contains a reverse transcriptase. The compounds which turned out to be inhibitors with SR-D were then tested with the human immune-deficiency virus HIV to verify their effect with this virus. Both virus systems exhibit comparable results supporting the usefulness of the SR-D model virus which does not require biohazard precautions.

The usefulness of the here described compounds is analyzed first in a system containing SR-D associated reverse transcriptase and in addition synthetic poly(rA) as template, oligo(dT)$_{10}$ as primer, and the four deoxyribonucleotides dATP, dGTP, dCTP, and ($^3$H)-TTP.

The inhibitors were added to the reaction mixtures. The compounds used are: foscarnet, suramin, chondroitin sulfate, DEAE-dextran (diethylamine ethyl-dextran), heparin, dextran, dextran sulfate MW 5000, dextran sulfate MW 8000, dextran sulfate MW 500,000, or pentosan polysulfate MW 5000. Chondroitin sulfate is a high-molecular weight mucopolysaccharide, which consists of esters of glucoronic acid or iduronic acid, and esters of chondrosamine with H$_2$SO$_4$. Heparin is a high-molecular weight mucopolysaccharide which can be isolated from animal organs and is composed of D-glucosamine residues.

The efficiency of the polymerase reaction is defined by the amount of ($^3$H)-TMP incorporated into DNA synthesized. Results of such an experiment are presented in FIGS. 1A and B.

The compounds dextran sulfate MW 500,000 and MW 8000 are efficient inhibitors. Somewhat less inhibitory are the effects of foscarnet, suramine and pentosan polysulfate MW 5000. Low inhibitory effect is exhibited by heparin, dextran, dextran sulfate MW 5000, DEAE-dextran, and chondroitin sulfate. The poor inhibition of the latter compounds is either due to an amino group (heparin), carboxyl group (chondroitin sulfate), positive charge (DEAE-dextran) or lack of negative charge (dextran). The low inhibition provided by dextran sulfate MW 5000 and the high inhibitory effect of pentosan polysulfate MW 5000 indicate that the inhibitory effect of the here described polymeric inhibitors which contain inorganic anionic groups does not correlate simply with the molecular weight of the polymers. The results indicate that the dextran sulfate in order to be useful for the purpose of the invention should have a molecular weight of more than 5000.

The superior properties of dextran sulfate MW 8000, MW 500,000, and pentosan polysulfate MW 5000 compared to others is further supported by their efficiency index (LD$_{50}$/inhibitor concentration). The LD$_{50}$ values are known from the literature. Concentration of the inhibitors which block 90% and 99% of the polymerase activity is derived from FIGS. 1A and B. The calculated efficiency indices are summarized in Table I. They indicate that the efficiency index of the here described compounds is about 140 times higher than that of other so far known inhibitors of the reverse transcriptase (foscarnet, suramin).

FIGS. 1C and D show reactions performed with the synthetic polymer poly(dA). poly(dT) (a synthetic analog of double-stranded DNA) which detect the reverse transcriptase-associated DNA-dependent DNA polymerase activity. Also this enzyme activity is inhibited by the three most efficient inhibitors shown in FIGS. 1A and B, even though 10 times less efficiently. This reduced effect is of importance. It indicates that other DNA-dependent DNA polymerases, e.g. those of cellular origin, are less affected by the inhibitory effect of the here described compounds than the proper reverse transcriptase. This results in reduced side-effects on the normal cellular replication machinery.

Figure 2A:
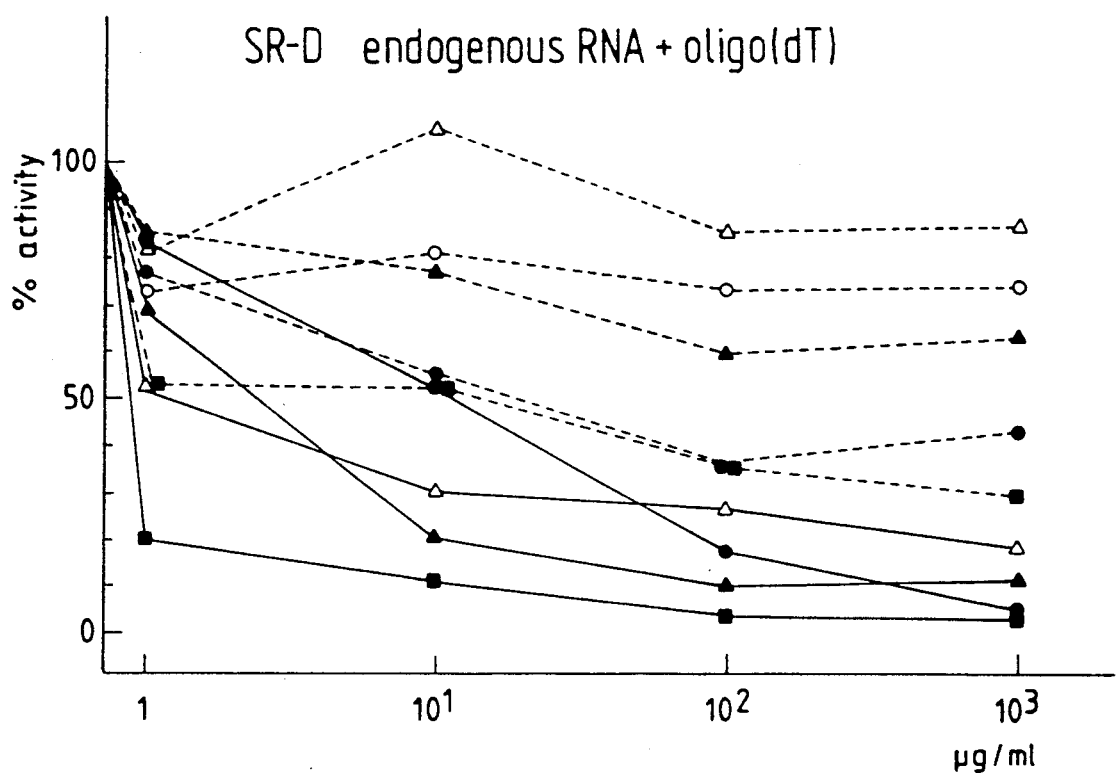
Figure 2B:
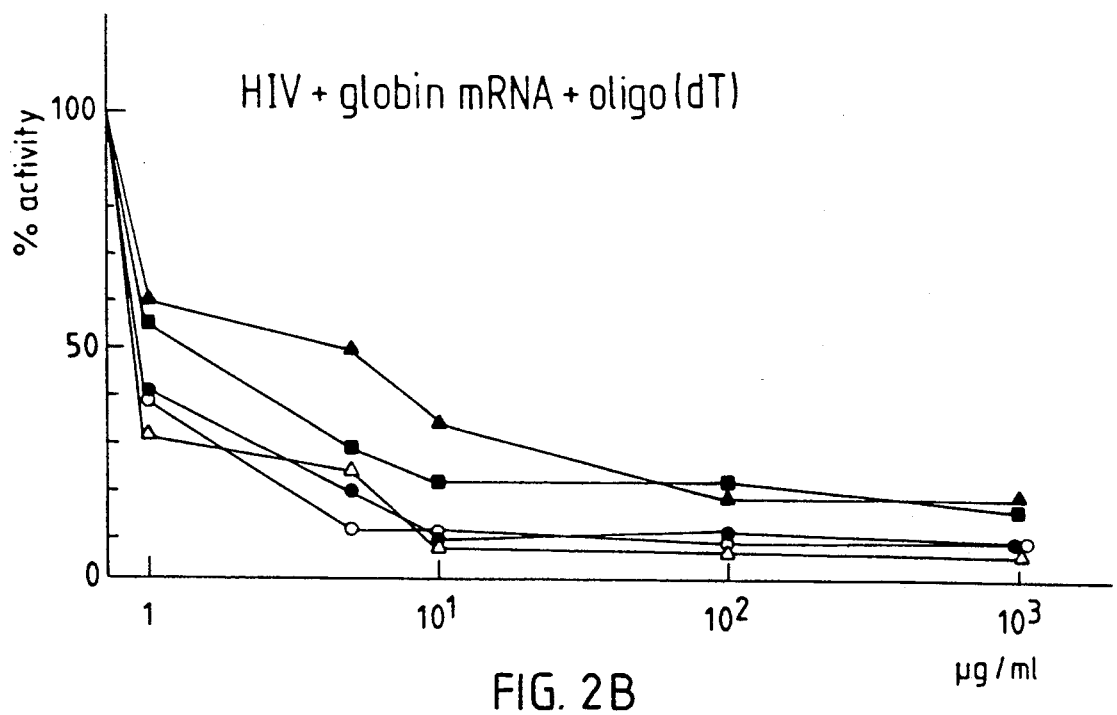
Figure 2C:
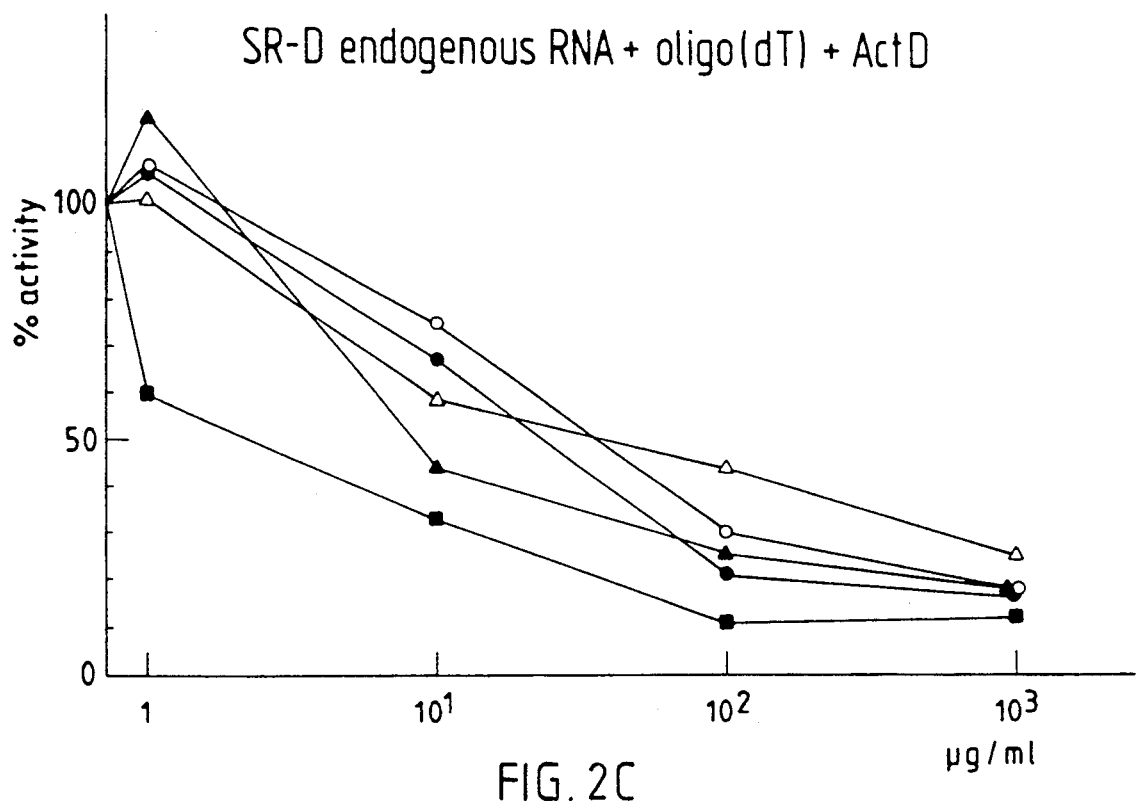

In addition, SR-D-associated reverse transcriptase activity can be determined using the endogenous viral RNA as template and synthetic oligo(dT) as primer. The result of such a test is shown in FIG. 2A. The inhibitory compounds are further shown to also block HIV-associated reverse transcriptase. This test, however, requires exogenous globin mRNA as template, since this enzyme is partially purified and template-free (FIG. 2B). The effect of Actinomycin D on both of these experiments is shown in FIGS. 2C and D. Actinomycin D blocks DNA-dependent DNA synthesis without affecting the actual reverse transcription of RNA into DNA.

The mechanism of the inhibition exhibited by the here described compounds is still not fully clear; probably it is based on the fact that the organic polymers contain inorganic anionic groups which mimick single-stranded nucleic acids, the natural substrates of the reverse transcriptase.

The here described compounds can be administered in the form of customary medicaments, e.g. solutions, coated tablets, tablets, capsules, or solutions for injection or infusion, orally or parenterally, e.g. intramuscularly or intravenously. The dose depends on the specific compound to be used and the weight of the patient. The daily doses administered are in the case of dextran sulfate MW 8,000 or MW 500,000 and in the case of pentosane polysulfate MW 5,000 10 mg to 10 g with the normal drug forms and 5 mg to 10 g on parenteral administration.

It is possible to use customary vehicles and additives for the preparation of medicaments containing the here described compounds. Examples of the customary vehicles are water, physiological saline, alcohols, polyethylene glycols, glycerol esters, gelatine, carbohydrates, such as lactose and starch, magnesium stearate and talk. Examples of customary additives are preservatives, sterilizing agents, lubricants, wetting agents and emulsifiers, colorants, masking flavors and aromatic substances. The selection of the vehicles and additives depends on whether the formulations are to be administered orally or parenterally. The dextran sulfates and pentosane polysulfates may also be formulated as pharmaceutical compositions, e.g. tablets, without the use of carriers or additives.

Legends to the Figures

FIG. 1: Inhibition of RNA-dependent DNA synthesis.

Figure 1D:
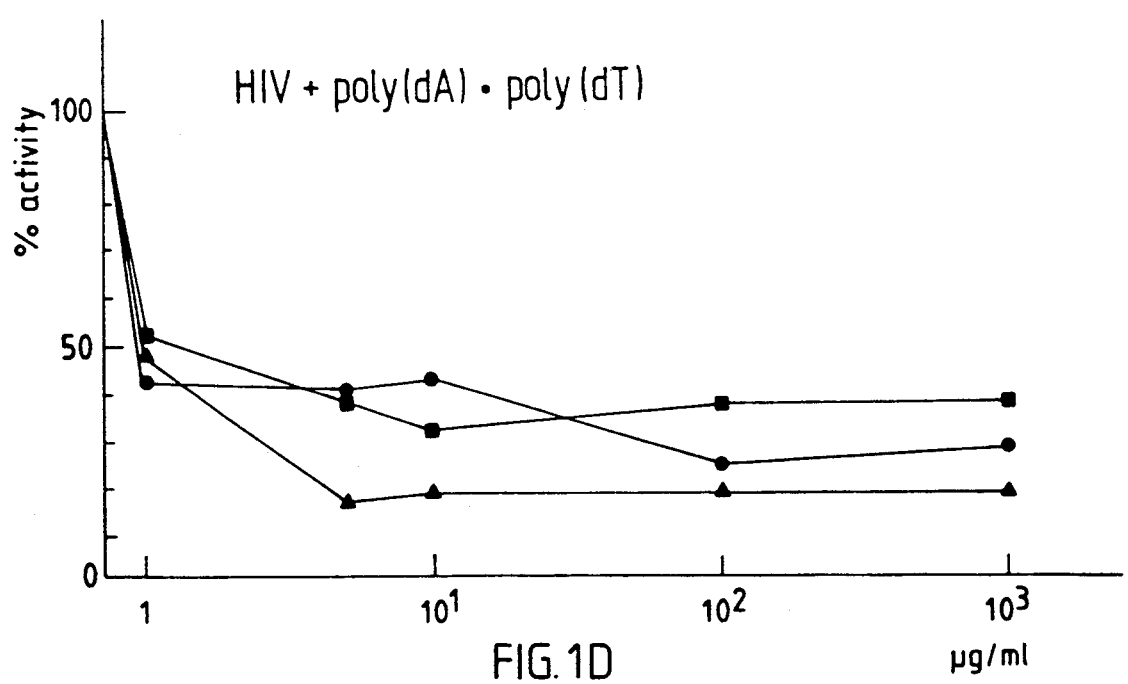

The inhibition of the SR-D-associated reverse transcriptase was tested using synthetic poly(rA) as template and synthetic oligo(dT) as primer and the following compounds: chondroitin sulfate (Δ---Δ), dextran (o---o), DEAE-dextran (Δ---Δ), dextran sulfate MW 5000 (●---●), heparin (■---■), pentosan polysulfate MW 5000 (Δ—Δ), suramin (●—●), foscarnet (o—o), dextran sulfate MW 8000 (Δ—Δ), dextran sulfate MW 500,000 (■—■) (FIG. 1A). The inhibition of the HIV-associated reverse transcriptase was analyzed using poly(rA) oligo(dT) only with those compounds of FIG. 1A which exhibited inhibitory effects (FIG. 1B). The inhibition of the DNA-dependent DNA polymerase activity associated with the reverse transcriptase was tested with SR-D plus poly(dA) poly(dT) (FIG. 1C), and HIV plus poly(dA) poly(dT) (FIG. 1D). Concentrations of the compounds ($\mu$g/ml) are indicated on the abscissa. DNA synthesis is measured by $^3$H-TMP (counts per minute, cpm) incorporation into acid precipitable DNA. The reduction of the incorporation by the inhibitors is expressed in % of the untreated control (100%) on the ordinate.

FIG. 2: Inhibition of RNA-dependent DNA synthesis.

Figure 2D:
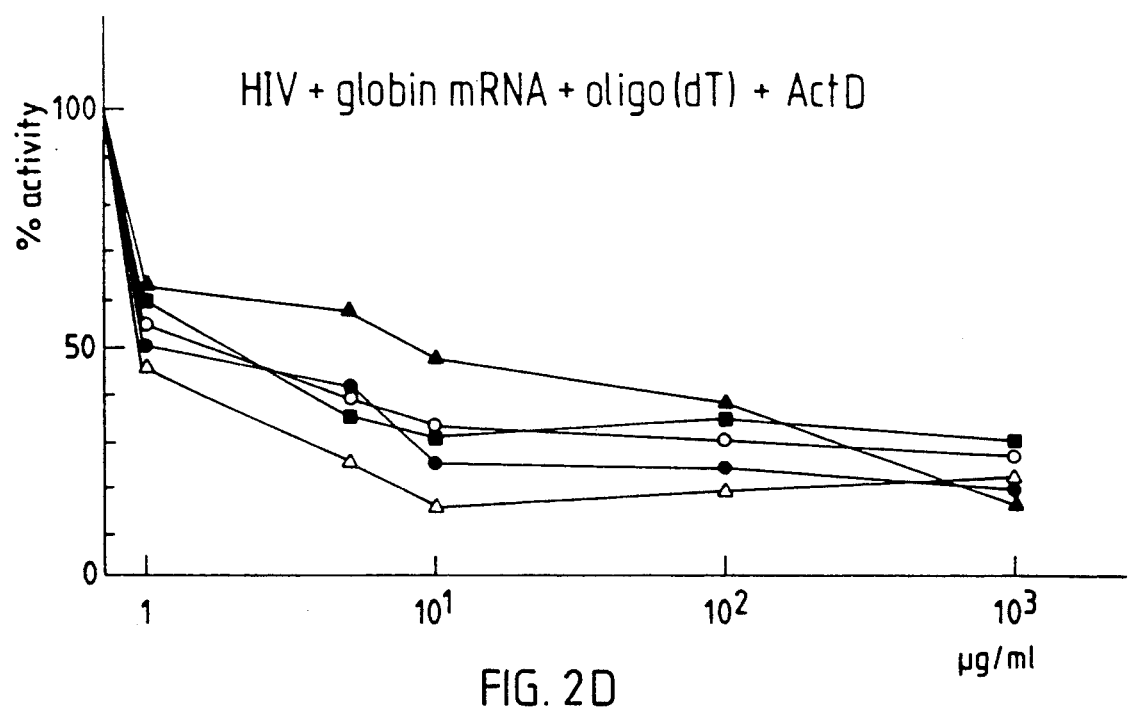

The inhibition of the SR-D-associated reverse transcriptase was tested with the endogenous viral RNA in the presence of an oligo(dT)$_{10}$ primer with all compounds listed in FIG. 1A, (FIG. 2A). HIV-associated reverse transcriptase is template-free and therefore requires the addition of exogenous globin mRNA plus oligo(dT)$_{10}$ primers. Only those inhibitors were used which according to FIG. 2A exhibited remarkable inhibitory effects (FIG. 2B). The effect of Actinomycin D on the reactions shown in FIG. 2A and FIG. 2B is shown in FIG. 2C and FIG. 2D respectively. Actinomycin D blocks double-stranded DNA - dependent DNA synthesis, but not RNA-dependent DNA synthesis.

The invention is further illustrated by the following non-limiting examples.

EXAMPLE I

The test viruses SR-D and HIV were isolated from tissue-culture supernatants. Conditions of the experiments were established with the SR-D reverse transcriptase and confirmed with that of HIV because of biohazard problems. The results confirm the known fact that reverse transcriptases of retroviruses resemble each other very closely.

(a) Isolation of the viruses:

Isolation of SR-D and HIV followed published procedures (see K. Moelling, "Characterization of Reverse Transcriptase and RNase H from Friend Murine Leukemia Virus", Virology 62 (1974), p. 46–59; "Further characterization of the Friend Murine Leukemia Virus Reverse Transcriptase-RNase H Complex", J. Virol. 18 (1976), p. 418–425; "Two Avian Sarcoma Virus Mutants with Defects in the DNA Polymerase-RNase H Complex", J. Virol. 32 (1979) p. 370–378). Normal chick embryo fibroblasts which are prepared according to standard techniques were infected with SR-D virus. The SR-D virus can be obtained from many laboratories or the American Type Tissue Collection (ATCC), Rockville, Md./U.S.A (ATCC VR 354). The HIV virus was recovered from HIV-infected H9 cells which were obtained through the courtesy of Dr. R. C. Gallo, NIH, Bethesda, Md./U.S.A. Culture supernatants were harvested every 24 hrs, clarified by low speed spon (10,000 rpm, 30 min, 4° C.) and kept frozen (−70° C.) A total of 5 liters of supernatant was collected, thawed, centrifuged as above and the virus pelleted (20,000 rpm, 2 hrs, 4° C. in SW27 rotor, Beckman Co.). The virus pellet was resuspended in about $10^{-3}\times$ the original volume (5 ml) of physiological buffer THE (0.05M Tris-HCl, pH 7, 0.1M NaCl, 0.005 M EDTA, pH 7). Subsequently the virus particles were centrifuged through a 20 to 70% sucrose gradient in THE (30,000 rpm, 8 hrs, 4° C., SW27 rotor, Beckman Co.). The virus was recovered at a density of 1.16 g/cm$^3$. The protein content was adjusted to 1 mg/ml with TNE and the virus stored frozen in aliquots. HIV virus was lysed as described below, diluted $10\times$ in TNE and passed over a DEAE-cellulose column to remove endogenous infectious RNA. The enzyme contained in the flow-through which represents the reverse transcriptase, was stored frozen in aliquots.

The SR-D virus was lysed in the presence of 0.8% Nonidet NP 40$^{(R)}$ (Fluka AG, Buchs, Suisse), 0.1M NaCl, 1 mM DTT (dithiothreitol) at about 0.5 to 1 mg/ml for 10 min at 4° C. and subsequently analyzed in an enzyme assay consisting of a total volume of 100 μl of: 50 mM Tris-HCl, pH 7.8, 8 mM MgCl$_2$ 80 mM KCl, 1 mM DTT, 20 mμmole each of dATP, dGTP, dCTP, and 0.2 mμmole of $^3$H-dTTP (50 Ci/mmole). The indicated templates were used in amounts of 10 μg per 100μl assay. They are stored at 10 mg/ml or 1 mg/ml in H$_2$O at −20° C. as stock solutions. Inhibitors were used at maximally 10 μl per 100 μl assay. The inhibitors foscarnet (Astra Lademedel AB, Sddertalje, Sweden) and suramin (Bayer, Leverkusen, West Germany) were tested in parallel. The assay lasted 60 min at 37° C. The reaction was terminated by the addition of 10% trichloroacetic acid (TCA, 0.5 ml). The DNA synthesized was precipitated by incubation for 20 min at 4° C. and subsequently recovered by filtration through membrane filters which removes the non-incorporated $^3$H-TMP. The radioactive DNA collected on the filter was counted by liquid scintillation counting and incorporated cpm determined. About 1000 cpm corresponding to 1% of the reaction was subtracted. The filters are washed repeatedly by 5% TCA (50 ml in total) and saturated pyrophosphate solution (10 ml).

$^3$H cpm incorporated in the DNA in the absence of inhibitors was defined as 100%. It corresponded to about 100,000 to 300,000 cpm per reaction. Increasing amounts of inhibitors were applied to the test. They are indicated as final concentration per assay in μg/ml.

EXAMPLE 2

Inhibition of reverse transcriptase

As efficient template-primers of the reverse transcriptase synthetic substances such as poly(rA).oligo(dT)$_{10}$ (Boehringer, Mannheim, Germany) can be used which mimick natural RNA and primer molecules. A stock-solution of 1 mg/ml can be stored frozen. 5 to 10 μg per 100 μl reaction are used. The assay is performed as described in Example 1. Results of this assay performed with the inhibitors foscarnet, suramin, chondroitin sulfate, DEAE-dextran, heparin, dextran, dextran sulfate MW 5000, MW 8000, and MW 500,000 or pentosan polysulfate MW 5000 are shown in FIG. 1A using SR-D. Only those compounds which act as inhibitors are tested with HIV as well, shown in FIG. 1B (for details, see legend).

The results shown in FIGS. 1A and B allow to determine the concentration of the inhibitors which result in 90% or 99% inhibition. The quotient of the LD$_{50}$ values (taken from published literature) and the inhibitor concentrations indicated in FIG. 1 is the efficiency index shown in Table I.

TABLE I

| Compound | LD$_{50}$[1] [mg/Kg] | Efficiency index[3] 99% (inhibition derived from FIG. 1) | 90% (inhibition derived from FIG. 1) |
|---|---|---|---|
| Inhibitors of the invention | | | |
| dextran sulfate MW 500,000 | 150 | 1.5 | 200 |
| dextran sulfate MW 8,000 | 2000 | 20 | 270 |
| pentosan polysulfate MW 5,000 | 1000 | 1 | 20 |
| Known Inhibitors | | | |
| suramin | 40 | 0.4 | 2 |
| foscarnet | 500[2] | 1 | 25 |

[1]LD$_{50}$ of dextransulfate MW 500,000 and MW 8000 is known from Br. J. of Pharmacology 9, 1 (1954), Table S.5–10. The LD$_{50}$ of pentosanpolysulfate is known from a data sheet of Bene Chemie GmbH;
[2]calculated from MW;
[3]efficiency index is defined as LD$_{50}$/inhibitor concentration.

Table I indicates that the here described compounds exhibit an efficiency index which is up to 140 times higher than that of the known compounds suramin and foscarnet.

EXAMPLE 3

Inhibition of reverse transcriptase-associated DNA-dependent DNA polymerase activity. The reverse transcriptase exhibits several activities, an RNA-dependent and a DNA-dependent DNA polymerase activity. The latter activity is tested using synthetic polymers, poly(dA) poly(dT). All other conditions are identical to details described in example 1 and 2. The compounds tested for inhibition are listed in the legend to FIG. 1 (C) and (D). Their effect on this activity is about 10 times less than the effect on RNA-dependent DNA polymerase activity. DNA-dependent DNA polymerases are present in normal cells as well and should be less affected than the reverse transcriptase so that the side effects on normal cells is lower.

EXAMPLE 4

Inhibition of endogenous or RNA-dependent DNA synthesis in absence and presence of Actinomycin D. The viral RNA which is identical to the viral mRNA is the most specific template of any reverse transcriptase. Addition of oligo(dT) primers stimulates the transcription up to 10 fold. If the endogenous RNA has been removed as is the case for HIV, any natural mRNA (which is DNA-free) can serve as template. Again oligo(dT)$_{10}$ is supplemented to offer start sequences. Transcription from RNA into DNA will take place first but subsequently also DNA in double-stranded DNA can be synthesized. This latter reaction can be specifically inhibited by Actinomycin D, an intercalating antibiotic. Therefore, in the presence of Actinomycin D the reverse transcriptase reaction itself will be measured only.

Test reactions with the compounds were performed as described in examples 2 and 3 (FIGS. 2A and B). Actinomycin D (Boehringer Mannheim) (1 mg/ml stock solution kept stored at $-20°$ C. in the dark) was added to 10 μg/ml final concentration during the assay (FIG. 2C and D). The compounds tested are listed in the legends. Globin mRNA (5 μg per assay) was purchased from Boehringer Mannheim. It is solubilized at 1 mg/ml and stored frozen. The observed inhibitory effects are very alike with the various tests described in examples 1 through 3.

EXAMPLE 5

Tablets containing dextran sulfate MW 8,000

To prepare tablets, 20 g dextran sulfate MW 8,000 are granulated, thoroughly mixed with 78 g lactose and 2 g calcium stearate and the mixture is compressed in a tabletting machine to form tablets, each weighing 1000 mg and containing 200 mg of the dextran sulfate.

What is claimed is:

1. A method for prophylaxis or therapeutic treatment of retrovirus infections of mammals which comprises administering to a mammal requiring said prophylaxis or treatment a polymeric carbohydrate containing sulfate groups but no carboxyl (—COOH) or amino (—NH$_2$) groups in an amount sufficient to provide efficient prophylactic or therapeutic effects against retrovirus infections.

2. The method according to claim 1, wherein the polymeric carbohydrate is composed of monomeric pentoses.

3. The method according to claim 1, wherein the polymeric carbohydrate is composed of monomeric hexoses.

4. The method according to claim 2 or 3, wherein the polymeric carbohydrate is composed of pyranose units having 5 or 6 carbon atoms.

5. The method according to claim 4, wherein the pyranose units are xylopyranose groups.

6. The method according to claim 4, wherein the pyranose units are glucopyranose groups.

7. The method according to claim 5, wherein the polymeric carbohydrate is a pentosane polysulfate.

8. The method according to claim 7, wherein the polymeric carbohydrate is pentosane polysulfate MW 5,000.

9. The method according to claim 6, wherein the polymeric carbohydrate is a dextran sulfate with a molecular weight of at least 6,000.

10. The method according to claim 9, wherein the polymeric carbohydrate is dextran sulfate MW 8,000.

11. The method according to claim 9, wherein the polymeric carbohydrate is dextran sulfate MW 500,000.

* * * * *